(12) United States Patent
Najafi et al.

(10) Patent No.: US 9,498,130 B2
(45) Date of Patent: Nov. 22, 2016

(54) WIRELESS DEVICE AND SYSTEM FOR MONITORING PHYSIOLOGIC PARAMETERS

(75) Inventors: Nader Najafi, Ann Arbor, MI (US); Sonbol Massoud-Ansari, El Dorado Hills, CA (US); Collin Anderson Rich, Ypsilanti, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 2150 days.

(21) Appl. No.: 12/399,131

(22) Filed: Mar. 6, 2009

(65) Prior Publication Data

US 2009/0182206 A1 Jul. 16, 2009

Related U.S. Application Data

(62) Division of application No. 10/677,674, filed on Oct. 2, 2003, now Pat. No. 7,686,762.

(51) Int. Cl.
*A61B 5/02* (2006.01)
*A61B 5/00* (2006.01)

(52) U.S. Cl.
CPC ............ *A61B 5/0031* (2013.01); *A61B 5/6882* (2013.01); *A61B 2560/0219* (2013.01)

(58) Field of Classification Search
CPC .............. A61B 5/0031; A61B 5/6882; A61B 2560/0219

USPC ............ 600/481, 483–489, 508, 513; 607/23
See application file for complete search history.

(56) References Cited

U.S. PATENT DOCUMENTS 6,328,699 B1 * 12/2001 Eigler et al. .................. 600/486
6,409,674 B1 * 6/2002 Brockway et al. ........... 600/486
6,970,742 B2 * 11/2005 Mann et al. .................... 607/23

* cited by examiner

*Primary Examiner* — Tiffany Weston
(74) *Attorney, Agent, or Firm* — Hartman Global IP Law; Gary M. Hartman; Domenica N. S. Hartman

(57) ABSTRACT

A system for monitoring blood pressure and other physiologic parameters is provided. The system is designed such that it can be delivered to the patient with ease and minimal invasion. The system contains at least one self contained implantable sensing device consisting of a sensor, an electrical circuit for signal conditioning and magnetic telemetry, a biocompatible outer surface and seal, an anchoring method, and an external readout device. The implant is small in size so that it may be delivered to the desired location and implanted using a catheter, although direct surgical implantation is also possible. The circuit, sensor, and antenna for telemetry are packaged together and sealed hermetically to the biologic environment. The larger readout unit remains outside the body but proximal to the implant for minimizing communication distance.

18 Claims, 2 Drawing Sheets

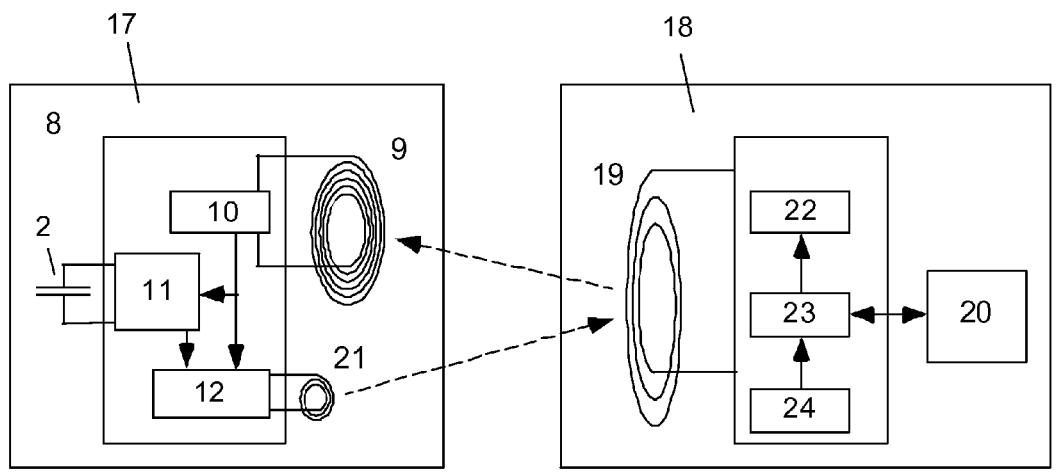
Figure 3
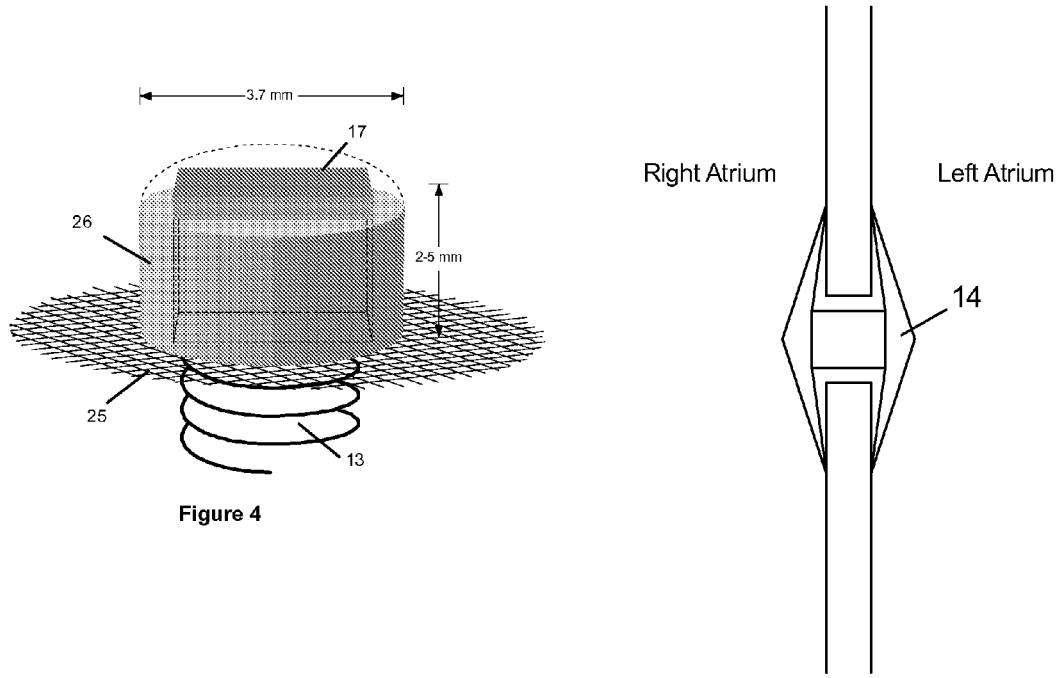
Figure 4
Figure 5

WIRELESS DEVICE AND SYSTEM FOR MONITORING PHYSIOLOGIC PARAMETERS

CROSS REFERENCE TO RELATED APPLICATIONS

This application is a Division of co-pending U.S. patent application Ser. No. 10/677,674 filed Oct. 2, 2003, which claims the benefit of U.S. Provisional Applications No. 60/415,537 filed Oct. 3, 2002, Ser. No. 60/415,538 filed Oct. 3, 2002, Ser. No. 60/416,406 filed Oct. 7, 2002, Ser. No. 60/416,407 filed Oct. 7, 2002, Ser. No. 60/416,408 filed Oct. 7, 2002, and Ser. No. 60/416,409 filed Oct. 7, 2002.

FIELD OF THE INVENTION

This invention relates generally to medical devices monitoring blood pressure and other physiologic parameters.

BACKGROUND OF THE INVENTION

A number of different physiologic parameters are strong candidates for continuous monitoring, such as blood pressure or flow, cardiovascular pressure, intracranial pressure, intraocular pressure, glucose levels, etc. Wireless sensors in particular are highly desirable for biologic applications because the transcutaneous passage of wires (or other communication "tethers") risks both infection to the patient and physical injury or device damage if the communication link experiences excessive pulling force.

A large number of proposed schemes for non-medical wireless communication rely on magnetic coupling between an electrical coil in an implanted device and a separate, external "readout" coil. One method of wireless communication well-known to those knowledgeable in the art is that of the LC tank resonator. A series-parallel connection of a capacitor and inductor has a specific resonant frequency ideally expressed as $1/\sqrt{LC}$, which can be measured from the impedance of the circuit. If one element of the inductor-capacitor pair varies with some physical parameter (e.g. pressure), while the other element remains at a known value, the physical parameter may be determined from the resonant frequency. For example, if the capacitor corresponds to a capacitive pressure sensor, the capacitance may be back-calculated from the resonant frequency. The sensed pressure may then be deduced from the capacitance by means of a calibrated pressure-capacitance transfer function.

The impedance of the LC tank may be measured directly or it may also be determined indirectly from the impedance of a separate readout coil that is magnetically coupled to the internal coil. The latter case is most useful for biologic applications in that the sensing device may be subcutaneously implanted, while the readout coil may be located external to the body, but in a location that allows magnetic coupling between the implant and readout coil. It is possible for the readout coil (or coils) to simultaneously excite the implant resonator and sense the impedance reflected back to the readout coil. Consequently, this architecture has the substantial advantage of requiring no internal power source, which greatly improves its prospects for long-term implantation (e.g. decades to a human lifetime).

Such devices have been proposed in various forms for many applications. Chubbuck (U.S. Pat. No. 4,026,276), Bullara (U.S. Pat. No. 4,127,110), and Dunphy (U.S. Pat. No. 3,958,558) disclose various devices initially intended for hydrocephalus applications (but also amenable to others) that use LC resonant circuits. The '276, '110, and '558 patents, although feasible, do not take advantage of recent advances in silicon (or similar) microfabrication technologies. Kensey (U.S. Pat. No. 6,015,386) discloses an implantable device for measuring blood pressure in a vessel of the wrist. This device must be "assembled" around the vessel being monitored such that it fully encompasses the vessel, which may not be feasible in many cases. In another application, Frenkel (U.S. Pat. No. 5,005,577) describes an implantable lens for monitoring intraocular pressure. Such a device would be advantageous for monitoring elevated eye pressures (as is usually the case for glaucoma patients); however, the requirement that the eye's crystalline lens be replaced will likely limit the general acceptance of this device.

In addition to the aforementioned applications that specify LC resonant circuits, other applications would also benefit greatly from such wireless sensing. Han, et al. (U.S. Pat. No. 6,268,161) describe a wireless implantable glucose (or other chemical) sensor that employs a pressure sensor as an intermediate transducer (in conjunction with a hydrogel) from the chemical into the electrical domain.

For example, the treatment of cardiovascular diseases such as Chronic Heart Failure (CHF) can be greatly improved through continuous and/or intermittent monitoring of various pressures and/or flows in the heart and associated vasculature. Porat (U.S. Pat. No. 6,277,078), Eigler (U.S. Pat. No. 6,328,699), and Carney (U.S. Pat. No. 5,368,040) each teach different modes of monitoring heart performance using wireless implantable sensors. In every case, however, what is described is a general scheme of monitoring the heart. The existence of a method to construct a sensor with sufficient size, long-term fidelity, stability, telemetry range, and biocompatibility is noticeably absent in each case, being instead simply assumed. Eigler, et al., come closest to describing a specific device structure although they disregard the baseline and sensitivity drift issues that must be addressed in a long-term implant. Applications for wireless sensors located in a stent (e.g., U.S. Pat. No. 6,053,873 by Govari) have also been taught, although little acknowledgment is made of the difficulty in fabricating a pressure sensor with telemetry means sufficiently small to incorporate into a stent.

Closed-loop drug delivery systems, such as that of Feingold (U.S. Pat. No. 4,871,351) have likewise been taught. As with others, Feingold overlooks the difficulty in fabricating sensors that meet the performance requirements needed for long-term implantation.

In nearly all of the aforementioned cases, the disclosed devices require a complex electromechanical assembly with many dissimilar materials, which will result in significant temperature- and aging-induced drift over time. Such assemblies may also be too large for many desirable applications, including intraocular pressure monitoring and/or pediatric applications. Finally, complex assembly processes will make such devices prohibitively expensive to manufacture for widespread use.

As an alternative to conventionally fabricated devices, microfabricated sensors have also been proposed. One such device is taught by Darrow (U.S. Pat. No. 6,201,980). Others are reported in the literature (see, e.g. Park, et al., Jpn. J. Appl. Phys., 37 (1998), pp. 7124-7128; Puers, et al., J. Micromech. Microeng. 10 (2000), pp. 124-129; Harpster et al., Proc. $14^{th}$ IEEE Int'l. Conf. Microelectromech. Sys. (2001), pp. 553-557).

Past efforts to develop wireless sensors have typically been limited to implant-readout separation distances of 1-2 cm, rendering them impractical for implantation much below the cutaneous layer. This would eliminate from consideration applications such as heart ventricle pressure monitoring or intracranial pressure monitoring, which require separation distances in the range of 5-10 cm. In the present state-of-the-art, several factors have contributed to this limitation, including: 1) signal attenuation due to intervening tissue, 2) suboptimal design for magnetic coupling efficiency; and 3) high internal energy losses in the implanted device.

SUMMARY OF THE INVENTION

It is an object of this invention to provide a system for chronic monitoring of blood pressure and other physiological parameters.

It is also an object of this invention to provide a system including an implantable device for monitoring blood pressure and other physiologic parameters that is delivered to the patient with ease and minimal invasion.

It is also an object of this invention to provide a method for delivering an implantable device for monitoring blood pressure and other physiologic parameters that is delivered to the patient with ease and minimal invasion.

The above objects are achieved by providing at least a self-contained implant comprising a sensor, an electrical circuit for signal conditioning and magnetic telemetry, and an antenna for telemetric communication with an external reader device. The implant is small in size so that it may be delivered to the desired location and implanted using a catheter, although direct surgical implantation is also possible. The circuit, sensor, and antenna are packaged together in the implant, which is preferably a small volume and sealed hermetically to the biologic environment. The larger reader device remains outside the body but can be placed proximal to the implant for minimizing communication distance.

BRIEF DESCRIPTION OF THE DRAWINGS

FIG. 3 is a block diagram of a magnetic telemetry based physiologic monitoring system according to a preferred embodiment of the present invention.

FIG. 4 is a perspective view of a sensor implant incorporating a screw anchoring mechanism.

FIG. 5 is a side view of a sensor implanted in the atrial septum according to a preferred embodiment of the present invention.

DETAILED DESCRIPTION OF PREFERRED AND ALTERNATE EMBODIMENTS OF THE INVENTION

Figure 1:
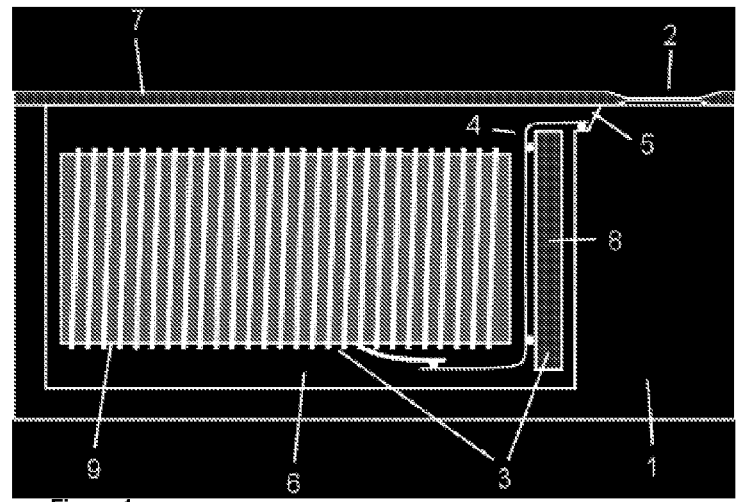
FIG. 1 is a side view of a miniature sensor module according to a preferred embodiment of the present invention.

The following description of preferred embodiments and methods provides examples of the present invention. The embodiments discussed herein are merely exemplary in nature, and are not intended to limit the scope of the invention in any manner. Rather, the description of these preferred embodiments and methods serves to enable a person of ordinary skill in the relevant art to make, use and perform the present invention.

The preferred communication scheme for the present invention, shown in FIG. 3, is based on magnetic telemetry. Without an external reader 18 present, an implant 17 lies passive and without any internal means to power itself. When a reading from a sensor 2 of the implant 17 is desired, the reader 18 is brought into a suitable range to the implant 17. The reader 18 then creates an RF (Radio Frequency) magnetic field large enough to induce sufficient voltage across an implant coil 9. When such a sufficient voltage exists across the implant coil 9, the implant circuit 8 may rectify the alternating waveform to create a direct voltage, which analog and/or digital circuitry may use as a power supply. At this point the implant 17 can be considered alert and, in the preferred embodiment, also ready for commands from the reader 18.

Once the direct voltage in the implant 17 has been established for the circuit operation, a number of techniques may be used to convert the sensor output into a form suitable for transmission back to the reader 18. In the preferred embodiment, a capacitive pressure sensor 2 and sigma delta conversion or capacitance to frequency conversion of the sensor output may be easily used. Capacitive sensors are preferred due to the small power requirements for electronics when reading capacitance values. Many pressure sensors are based on piezoresistive effects and, while suitable for some applications, do suffer in this application due to the higher power levels needed for readout. Sigma delta converters are preferred due to the tolerance of noisy supply voltages and manufacturing variations.

As those skilled in magnetic telemetry are aware, a number of modulation schemes are available for transmitting data via magnetic coupling. The preferred schemes include but are not limited to amplitude modulation, frequency modulation, frequency shift keying, phase shift keying, and also spread spectrum techniques. The preferred modulation scheme may be determined by the specifications of an individual application, and is not intended to be limited under this invention.

In addition to the many available modulation techniques are the many technologies developed that allow the implant 17 to communicate back to the reader 18 the signal containing pressure information. It is understood that the reader 18 may transmit either a continuous level of RF power to supply the implant's needed energy, or it may pulse the power allowing temporary storage in a battery or capacitor device. Similarly, the implant 17 of FIG. 3 may signal back to the reader 18 at any interval in time, delayed or instantaneous, during reader RF transmission or alternately in the absence of reader transmission. The implant 17 may include a single coil antenna 9 for both reception and transmission, or it may include two antennas, one each for transmission 21 and reception 9.

The preferred embodiment of the invention is based on a small inner package, preferably of glass and silicon, that can be fit with a number of shell options for various implantation methods. The cross-section in FIG. 1 illustrates a glass and silicon package for the miniature implant 17 according to a preferred embodiment of the invention. As illustrated in FIG. 1, the implant 17 includes a substrate 1, the sensor 2, and electronics 3 (both coil 9 and integrated circuit die 8 included in electronics). A secondary and optional substrate 4 may be used for attaching the various electronic components to each other and to sensor connections. An alternative preferred method is to use a cylindrical shaped package, made from silicon, glass, ceramic, metal, plastic, or any combination thereof which houses the coil and the electronic components. The miniature sensor 2 can either be fabricated separately and attached to the cylindrical package or may be directly fabricated onto the substrate 1. Note that the shell may be a separately fabricated piece into which the sensor 2 is placed; or it may be directly fabricated on the implant 17 (or some portion thereof); or it may be integral to the inner package, being only defined by a change in material.

The purpose of the shell is to simplify fabrication by allowing different processes, process flows, materials, and/or structures to be used for the subassembly (e.g. MEMS technologies) and the shell (e.g. machining and/or molding of plastics, glass, metals, rubbers, polymers, etc.) In some applications, the material of the implant 17 compatible with the environment, in which case a shell is not required and the implant 17 is the complete implantable sensing device.

The miniature sensor 2 can be any suitable miniature sensor adapted to detect and/or monitor various physiological parameters. For example, the sensor 2 can comprise a pressure sensor, a temperature sensor, a flow sensor, a velocity sensor, or a sensor adapted to measure specific chemistries such as gas content (e.g., $O_2$ and $CO_2$) and glucose levels. Various specific examples of these types of miniature sensors are known to those skilled in the art, and any one or more of these suitable sensors can be utilized in the sensor module of the present invention. While the specific type of sensor(s) chosen will depend on the application of the implantable system, the sensor(s) 2 should be of a sufficiently small size in order to facilitate placement within a catheter for delivery and implantation.

In the preferred embodiment of the implant 17 shown in FIG. 1, the bottom substrate 1 defines a cavity 6 in which the electronics 3 may be placed. With cubic geometry, the rigid substrate cavity walls enclose the electronics 3 on five of the six possible sides. Also in a preferred embodiment, at least part of the sensor 2 is disposed on the top side of the bottom substrate 1. Connections 16 to the sensor 2 may be made in a substrate recess 5 (recess is optional for increased clearance, and connection may alternately be co-planar with or above the plane of the substrate) adjoining the larger cavity 6, or through alternate lead transfer techniques in the substrate cavity 6.

A top substrate 7 is attached to the bottom substrate 1 to form a hermetic seal around the sensor 2 and electronics. In a preferred embodiment, the physically interacting parts of the sensor 2 are formed in the top substrate 7 and complete the sensor structure after subsequent processing steps after bonding. The two substrates 1 and 7 may be made of materials such as glass and silicon that are preferably anodically bonded together and provide excellent bond mechanical properties. Alternate methods of attachment include: fusion, frit, solder, laser welds, other welding, compression, thermal, thermal compression, eutectic, glue.

In a preferred arrangement, the electronics 3 are connected together via a rigid or flexible substrate, which may be either the bottom substrate 1 or a separate flexible substrate 4. The connection between the integrated circuit die 8 and the flexible substrate 4 is preferably made with flip-chip process to avoid the more fragile wire bonds. The circuit die 8 may include ASIC (Application Specific Integrated Circuits), capacitors, or diodes. The leads from the inductor coil 9 may fold over the flexible substrate 4 or be preformed for soldering to the substrate 4 with a preferably biocompatible solder such as gold-tin or silver-tin. The flexible substrate 4 may also extend to the connections 16 for the sensor 2, where the connection may be made with a number of methods such as silver epoxy, laser welding, solder, or other.

Figure 2:
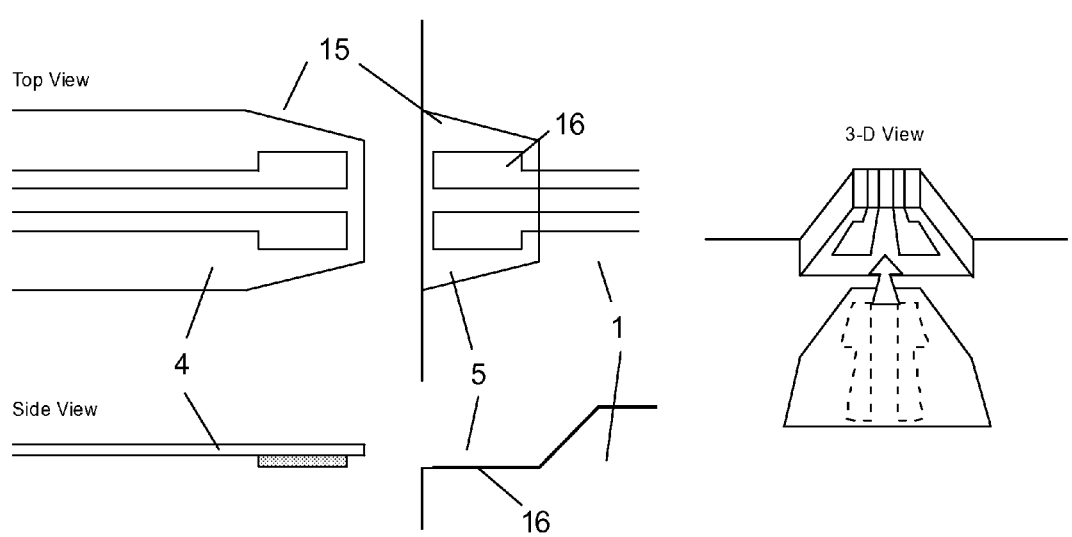
FIG. 2 is a top, side, and perspective view of a flexible substrate to rigid substrate self aligning connection illustrating a preferred arrangement of electrical leads within a substrate cavity.

Aligning the flexible substrate 4 to the bottom substrate recess 5 is shown in FIG. 2. A preferred structure to accommodate manufacturing tolerances matches complementary tapered shapes 15 of the recess 5 and the flexible substrate 4, ensuring that the electrical connections 16 are properly aligned. As the tapered shape 15 of the flexible substrate 4 is inserted into the recess 5, the electrical connections 16 are forced to align themselves to avoid faulty connections. Furthermore, any variance in the width of the tapered shapes 15 will be accommodated by a small variation in the final, lateral depth of insertion of the flexible substrate 4.

FIG. 3 illustrates a block diagram for the electronics 3 according to the present invention. The electronic circuit may consist of a receiving inductor coil 9, rectification circuitry 10, signal conditioning circuitry 11, and signal transmission circuitry 12.

A large number of possible geometries and structures are available for receiver coil and known to those skilled in the art. The coil conductor may be wound around a ferrite core to enhance magnetic properties, deposited on a flat rigid or flexible substrate, and formed into a long/skinny or short/wide cylindrical solenoid. The conductor is preferably made at least in part with a metal of high conductivity such as copper, silver, gold. The coil may alternately be fabricated on substrates 1, 4, or 8 (or any combination thereof) of FIG. 1. Methods of fabrication include sputtering, electroplating, lift-off, screen printing, and/or other suitable methods known to those skilled in the art.

The rectification circuitry 10 outputs a constant voltage level for the other electronics from an alternating voltage input. Efficient realizations of such circuitry are standard electronic techniques and may include full bridge diode rectifiers in the preferred embodiment. This rectification circuitry may include a capacitor for transient energy storage to reduce the noise ripple on the output supply voltage. This circuitry may be implemented on the same integrated circuit die with other electronics.

The signal conditioning circuit 11 processes an output signal from the sensor 2 and prepares it for transmission to an external receiving and/or analyzing device. For example, many pressure sensors output a capacitance signal that may be digitized for radio frequency (RF) transmission. Accordingly, the signal conditioning circuit places the output signal of the sensor into an appropriate form. Many different signal conditioning circuits are known to those skilled in the art. Capacitance to frequency conversion, sigma delta or other analog to digital conversion techniques are all possible conditioning circuits that may be used in a preferred embodiment.

The signal transmission circuitry transmits the encoded signal from the signal conditioning circuitry for reception by an external reader. Magnetic telemetry is again used for this communication, as the transmission circuitry generates an alternating electromagnetic field that propagates to the reader. Either the same coil 9 is used for signal reception and for transmission, or alternately a second coil 21 is dedicated for transmission only.

To limit the risk of thrombogenesis, the preferred embodiment has limited protrusion of volume into the blood stream, as both shape and size are factors in thrombogenesis. Another shell may be overmolded or preformed to house the glass/silicon module, and the outer shell contains the necessary apparatus for anchoring the implant. In a preferred embodiment, the outer shell may be formed with existing plastic injection technologies suitable for medical implantation. A coating, preferably of silicone, parylene and/or polymers provides a non-thrombogenic exterior for the biologic environment.

The implant may be located in various places depending on the blood pressure measurement of interest. For chronic heart failure the end-diastolic pressure may be of most importance, and therefore the left chambers of the heart or immediately attaching vessels may be preferred locations. Because the number of implants is not practically limited by the technology, multiple locations for blood pressure and/or other physiologic parameter measurements are easily established, including all chambers of the heart, major arteries and appendages. In the preferred embodiment, embedding the module in an area that does not significantly impede blood flow can minimize the thrombogenic effect of flow turbulence caused by this volume.

The implant may be modified with anchoring methods found on devices already used for implantation. Devices such as septal occluders, pacemaker leads, left atrial appendage occluders, etc. may be used as carriers for the current invention.

Pacemaker leads have a well-established history for implantation methods, and similar techniques are possible for the current invention. A screw 13 or barb may be used to attach the implant to a heart or vessel wall. In the first package option shown in FIG. 4, a screw may be molded into the device shell 26, and screwed into the ventricle wall so that the screw buries below the wall surface. In addition, the package may have mesh 25 attached to the device to promote tissue growth and anchoring.

A second package option can be attached with a metal tine or barb placed with a catheter. These devices work well in trabeculated areas of the heart, and therefore are used often for implanting pacing leads in the right ventricle. Clips or expanding probes may also be used, both of which would penetrate the heart or vessel wall slightly.

Devices have been made and approved by the FDA to occlude atrial septum defects (a septal occluder) and other vascular holes. An umbrella structure 14 may be folded inside a catheter for delivery and then expanded for implantation. In a preferred embodiment, the present invention may be anchored to the septum with similar techniques, as shown in FIG. 5. An important aspect of this preferred embodiment is that the majority of the implantable sensing device is located in the right side of the heart, with minimum protrusion in the left side of the heart. This embodiment will greatly reduce the thrombogenicity.

The readout device 18 includes an inductor 19 for communicating with and powering the implant 17 via magnetic telemetry. Also included is signal reception 24, signal processing 23, and transmission circuitry 22 for data analysis and subsequent communication. FIG. 3 illustrates the system diagram and the blocks of the reader. There are many techniques for construction of the reader coil and processing electronics known to those skilled in the art. The reader may interface to a display, computer, or other data logging device 20.

Note that in addition to sensing physiologic parameters, the described system could be augmented with various actuation functions. In such case, the implant device would augmented with any of various actuators, including but not limited to: thermal generators; voltage or current sources; probes, or electrodes; drug delivery pumps, valves, or meters; microtools for localized surgical procedures; radiation-emitting sources; defibrillators; muscle stimulators; pacing stimulators.

The foregoing disclosure includes the best mode devised by the inventors for practicing the invention. It is apparent, however, that several variations in the apparatuses and methods of the present invention may be conceivable by one skilled in the art. Inasmuch as the foregoing disclosure is intended to enable one skilled in the pertinent art to practice the instant invention, it should not be construed to be limited thereby, but should be construed to include such aforementioned variations.

We claim:

1. A miniature implant for measuring physiologic parameters for medical applications, the miniature implant comprising an implantable self-contained sensor module that is sized and configured to be entirely implanted within a living body and physically coupled to a wall of an internal organ of the living body, the sensor module comprising:
    a sensor adapted to sense a physiologic parameter of the living body;
    an inductor coil adapted to receive operating power from a magnetic field generated outside the living body;
    means for conditioning a sensor signal received from the sensor and generate therefrom a conditioned sensor signal;
    means for transmitting the conditioned sensor signal to a location outside the living body via magnetic telemetry;
    an outer shell that houses the inductor coil, the conditioning means and the transmitting means; and
    an anchoring mechanism exterior to the outer shell and adapted to physically couple the outer shell to the wall of the internal organ;
    wherein the miniature implant is adapted to be entirely implanted within the living body and solely positioned and anchored within the living body by the anchoring mechanism, and wherein the sensor module is sized and configured to be delivered and implanted with a catheter.

2. The miniature implant of claim 1 wherein the sensor module is sized and configured to be implanted using a minimally invasive outpatient technique.

3. The miniature implant of claim 1 wherein the anchoring mechanism is sized and configured to pass entirely through a septal wall of a heart, engage opposite surfaces of the septal wall, and clamp the sensor module to the septal wall.

4. The miniature implant of claim 3 wherein the septal wall is an atrial septum and the sensor module and the anchoring mechanism are sized and configured to pass entirely through the atrial septum.

5. The miniature implant claim 3 wherein the anchoring mechanism comprises two umbrella-shaped anchors that are sized and configured to engage opposite surfaces of the septal wall and clamp the septal wall therebetween.

6. The miniature implant claim 5 wherein the outer shell and the anchoring mechanism are coupled to each other and sized and configured so that a larger portion of the sensor module can be located in the right side of the heart and a relatively smaller portion of the sensor module can be located in the left side of the heart.

7. The miniature implant of claim 1 wherein the anchoring mechanism comprises a helical screw.

8. The miniature implant of claim 1 wherein the anchoring mechanism comprises an expandable tine that is sized and configured to implant the sensor module on a trabeculated area of the heart.

9. The miniature implant of claim 1 wherein the anchoring mechanism is made from one or more of nitinol, teflon, stainless steel, polymer, titanium, and biocompatible metals.

10. The miniature implant of claim 1 wherein at least a portion of the sensor module is coated with one or more layers of at least one coating material.

11. The miniature implant of claim 10 wherein the at least one coating material is at least one of silicone, hydrogels, parylene, polymer, nitrides, oxides, nitric-oxide generating materials, carbides, silicides, and titanium.

12. The miniature implant of claim 1, wherein the outer shell defines a cylindrical-shaped package.

13. A method of using the miniature implant of claim 1 in a medical application chosen from the group consisting of cardiovascular diseases, congestive heart failure, congenital heart diseases, diseases related to intracranial pressure, abdominal aortic aneurysm, intraocular pressure for eye related diseases urinary diseases, and gastrointestinal diseases.

14. The miniature implant of claim 1 wherein the sensor is adapted to sense pressure, temperature, flow, blood composition, blood gas content, chemical composition, acceleration, or vibration.

15. A method of using the miniature implant of claim 1 to monitor the physiologic parameter of the internal organ.

16. The method of claim 15 wherein the physiologic parameter is pressure.

17. The method of claim 15 wherein the internal organ is a heart, brain, kidney, lung, or abdomen.

18. The method of claim 15 wherein the pressure is left ventricular end diastolic pressure, left atrium pressure, left atrium appendage pressure, mean left atrium pressure, in the left side of the heart, in the right side of the heart, right atrium pressure, mean right atrium pressure, right ventricular end diastolic pressure, differential pressure between left and right atrium, intracranial pressure, or intraocular pressure.

* * * * *